United States Patent
Bedell et al.

(10) Patent No.: US 9,859,091 B1
(45) Date of Patent: Jan. 2, 2018

(54) AUTOMATIC ALIGNMENT FOR HIGH THROUGHPUT ELECTRON CHANNELING CONTRAST IMAGING

(71) Applicant: International Business Machines Corporation, Armonk, NY (US)

(72) Inventors: Stephen W. Bedell, Wappingers Falls, NY (US); Kunal Mukherjee, White Plains, NY (US); John A. Ott, Greenwood Lake, NY (US); Devendra K. Sadana, Pleasantville, NY (US); Brent A. Wacaser, Putnam Valley, NY (US)

(73) Assignee: International Business Machines Corporation, Armonk, NY (US)

( * ) Notice: Subject to any disclaimer, the term of this patent is extended or adjusted under 35 U.S.C. 154(b) by 5 days.

(21) Appl. No.: 15/187,476

(22) Filed: Jun. 20, 2016

(51) Int. Cl.
*H01J 37/28* (2006.01)
*H01J 37/147* (2006.01)
*G01N 23/207* (2006.01)
*G01N 23/203* (2006.01)

(52) U.S. Cl.
CPC ........ *H01J 37/1478* (2013.01); *G01N 23/203* (2013.01); *G01N 23/207* (2013.01); *G01N 2223/401* (2013.01); *H01J 2237/1506* (2013.01)

(58) Field of Classification Search
None
See application file for complete search history.

(56) References Cited

U.S. PATENT DOCUMENTS

| | | | | |
|---|---|---|---|---|
| 4,962,306 A | * | 10/1990 | Hodgson | H01J 37/244 250/305 |
| 5,408,098 A | * | 4/1995 | Wells | H01J 37/244 250/305 |
| 6,711,293 B1 | | 3/2004 | Lowe | |
| 2006/0231752 A1 | * | 10/2006 | Houge | H01J 37/295 250/306 |
| 2011/0108736 A1 | * | 5/2011 | Preikszas | H01J 37/1478 250/397 |
| 2012/0286159 A1 | * | 11/2012 | Donitz | H01J 37/28 250/309 |
| 2015/0369760 A1 | * | 12/2015 | Penman | G01N 23/203 250/307 |

OTHER PUBLICATIONS

Gutierrez-Urrutia et al., "Coupling of Electron Channeling with EBSD: Toward the Quantitative Characterization of Deformation Structures in the SEM", JOM, vol. 65, No. 9, 2013.*

(Continued)

*Primary Examiner* — Michael Logie
(74) *Attorney, Agent, or Firm* — Scully, Scott, Murphy & Presser, P.C.; Louis J. Percello, Esq.

(57) ABSTRACT

An automatic method is provided to align a semiconductor crystalline substrate for electron channeling contrast imaging (ECCI) in regions where an electron channeling pattern cannot be reliably obtained but crystalline defects need to be imaged. The automatic semiconductor crystalline substrate alignment method is more reproducible and faster than the current operator intensive process for ECCI alignment routines. Also, the automatic semiconductor crystalline substrate alignment method increases the throughput of ECCI.

20 Claims, 5 Drawing Sheets

(56) References Cited

OTHER PUBLICATIONS

Wilkinson, A.J., et al., "High resolution elastic strain measurement from electron backscatter diffraction patterns: New levels of sensitivity", Ultramicroscopy, Mar. 2006, pp. 303-313, 106.
Wright, S. I. "Fundamentals of automated EBSD", Electron Backscatter Diffraction in Materials Science, Springer US, 2000, 51-64.

* cited by examiner

AUTOMATIC ALIGNMENT FOR HIGH THROUGHPUT ELECTRON CHANNELING CONTRAST IMAGING

BACKGROUND

The present application relates to electron channeling contrast imaging (ECCI) of a crystalline material. More particularly, the present application relates to an automatic alignment method that can be used to increase the throughput during the ECCI of a crystalline material.

In the manufacturing of microelectronics, defects in the crystalline quality of the material can adversely affect device performance. As materials (such as, Ge, SiGe and/or III-V compound semiconductors) are added into the manufacturing line, defects caused by the epitaxy and processing of dissimilar materials become more abundant than with silicon only technologies. Therefore, it is important to test the crystal defect density in the materials in the line.

Conventional techniques used for such crystalline defect detection such as transmission electron microscopy or etchpit counting are destructive, since they require etching, cutting, polishing and/or thinning of the sample being tested.

Electron channeling contrast imaging (ECCI) is a scanning electron microscope (SEM) technique that can be used for such crystalline defect detection. One of the difficulties with existing ECCI is that it takes time to align and set up each scan to maximize contrast and acquire the most accurate images for ECCI analysis. In current ECCI, alignment is performed manually on each material being analyzed.

Further, in crystalline substrates that have been processed, there is the possibility of having very little or no areas available of sufficient requirements such that an electron channeling pattern can be collected to guide the setup of the channeling condition to be setup.

In view of the above, there is a need for providing a method to align the wafer for ECCI automatically and even when a reliable electron channeling map is not obtainable due to small size of the crystalline device areas.

SUMMARY

An automatic semiconductor crystalline substrate alignment method is provided to facilitate high throughput electron channeling contrast imaging (ECCI) of processed samples. The automatic semiconductor crystalline substrate alignment method of the present application is more reproducible and faster than the current operator intensive process for ECCI alignment routines. Moreover, the automatic semiconductor wafer alignment method of the present application can enable imaging of small regions that do not have readily accessible electron channeling patterns. In existing ECCI technology, a manual alignment is primarily performed on small pieces and on blanket samples only using the electron channeling pattern as a guide.

In one aspect of the present application, a method for automatic alignment that increases the throughput of ECCI is provided. In one embodiment of the present application, the method may include providing a substrate intentionally containing a plurality of spaced apart imageable ready regions capable of generating an electron channeling pattern or electron backscatter diffraction pattern surrounded by at least one device area containing a crystalline material that has a crystallographic orientation that aligned to the material of the imageable ready regions. Next, an image of the electron channeling pattern or electron backscatter diffraction pattern of each imageable ready region is obtained. Thereafter, an optimum channeling angle between the electron beam and the substrate is calculated at each imageable ready region using a first algorithm. The optimum channeling angle between and around each imageable ready region is then interpolated, using a second algorithm, to generate a map of the crystalline material present in the at least one device area.

DETAILED DESCRIPTION

Figure 1:
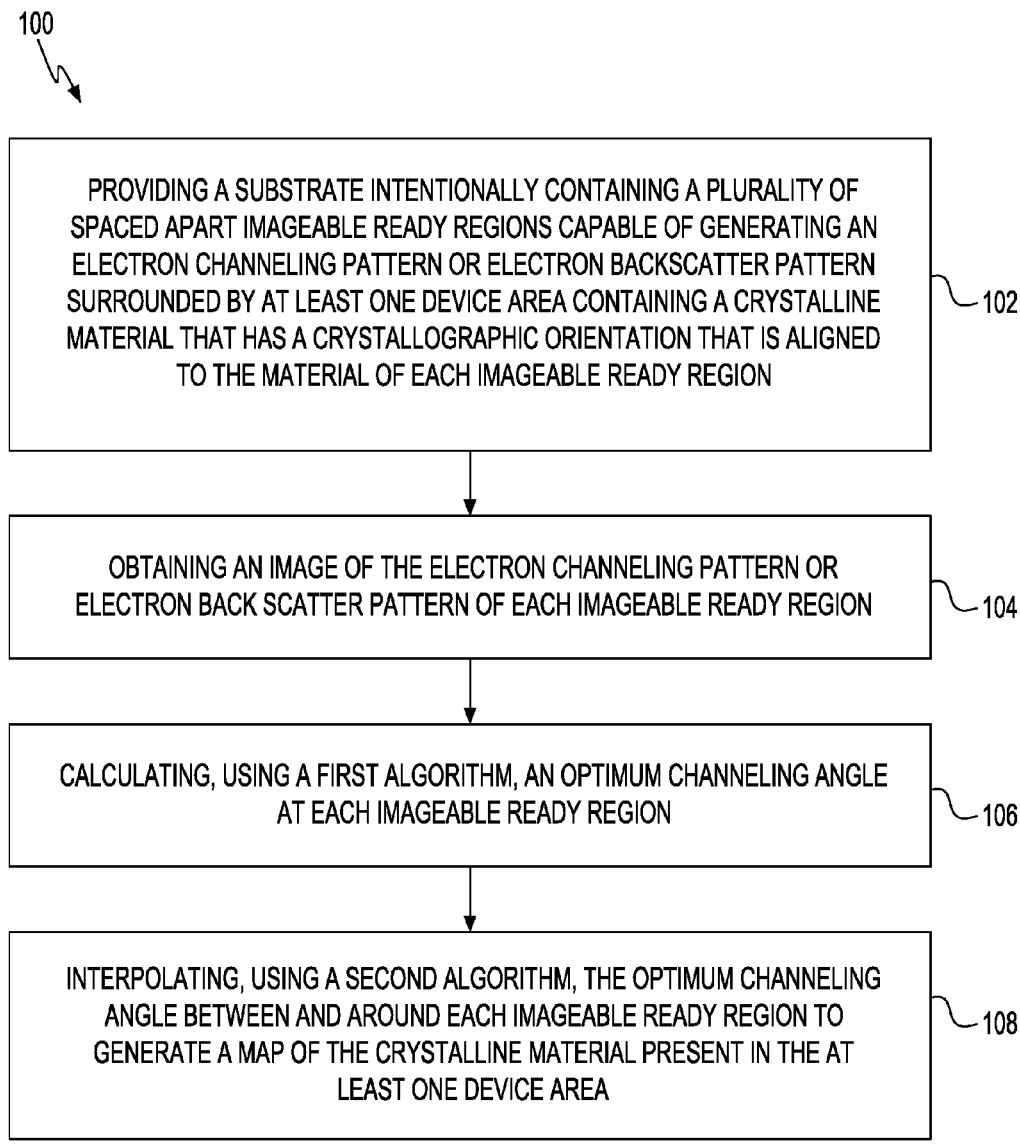
FIG. 1 is a flow diagram illustrating the basic processing steps that can be employed in one embodiment of the present application.

The present application will now be described in greater detail by referring to the following discussion and drawings that accompany the present application. It is noted that the drawings of the present application are provided for illustrative purposes only and, as such, the drawings are not drawn to scale. It is also noted that like and corresponding elements are referred to by like reference numerals.

In the following description, numerous specific details are set forth, such as particular structures, components, materials, dimensions, processing steps and techniques, in order to provide an understanding of the various embodiments of the present application. However, it will be appreciated by one of ordinary skill in the art that the various embodiments of the present application may be practiced without these specific details. In other instances, well-known structures or processing steps have not been described in detail in order to avoid obscuring the present application.

Reference is first made to FIG. 1 which represents a flow diagram 100 illustrating the basic processing steps that can be employed in one embodiment of the present application. Notably, FIG. 1 depicts a step 102 of providing a substrate intentionally containing a plurality of spaced apart imageable ready regions capable of generating an electron channeling pattern or electron backscatter diffraction pattern surrounded by at least one device area containing a crystalline material that that has a crystallographic orientation that is aligned to the material of the imageable ready regions by a known mathematical relationship. The flow diagram also includes a step 104 of obtaining an image of the electron channeling pattern or the electron backscatter pattern of each imageable ready region by conventional techniques such as scanning the electron beam across the region and recording the backscattered or secondary electron signal. The flow diagram 100 of FIG. 1 also shows a step 106 in which an optimum channeling angle between the electron beam and the substrate is calculated at each imageable ready region. The flow diagram 100 further includes a step 108 of interpolating, using a second algorithm, the optimum channeling angle between and around each imageable ready region to generate a map of the crystalline material present in the at least one device area. Each of these steps of the present application will now be described in greater detail.

Figure 2:
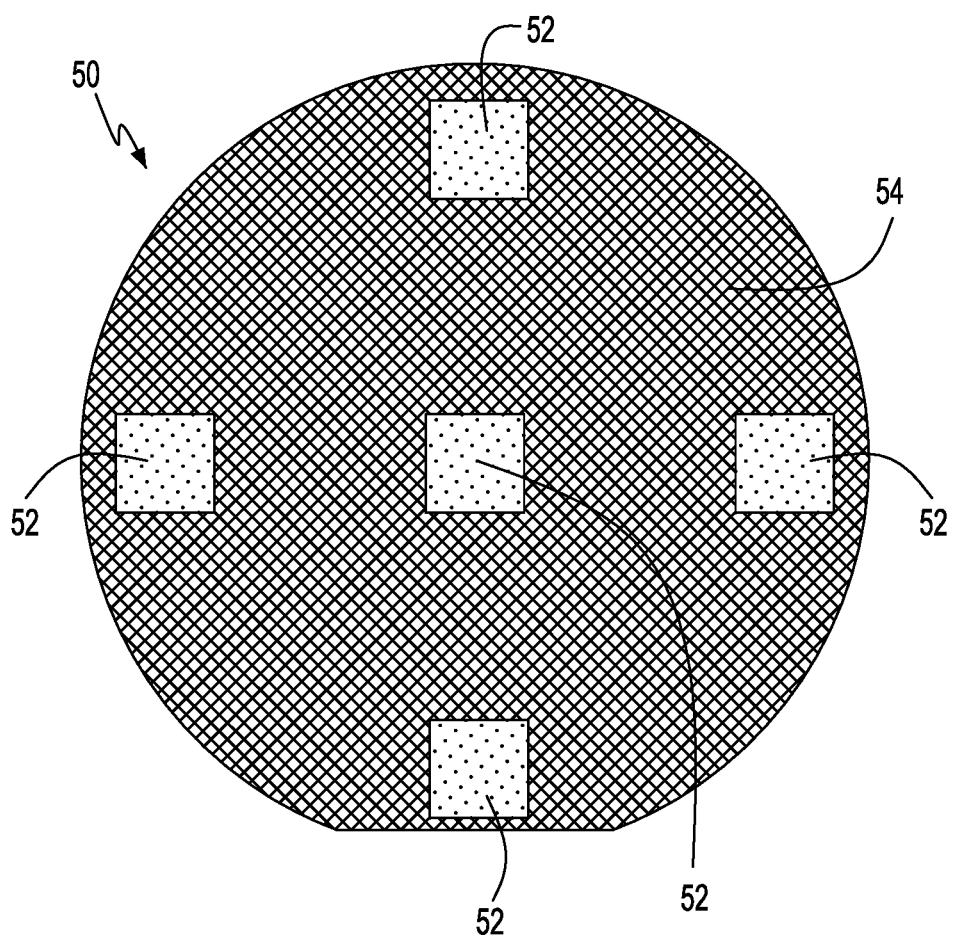
FIG. 2 is a top down view illustrating a semiconductor crystalline substrate containing a plurality of spaced apart imageable ready regions surrounded by at least one device area containing a crystalline material.

As indicated, the flow diagram 100 of FIG. 1 begins which step 102 that includes providing a substrate 50 that intentionally contains a plurality of spaced apart imageable ready regions 52 surrounded by at least one device area 54 containing a material that is linked to the crystalline material in each of the imageable ready region 52 by crystallography. Such a substrate 50 is shown in FIG. 2 of the present application. The imageable ready regions 52 are capable of generating either an electron channeling pattern or electron backscatter diffraction pattern.

The substrate 50 may include any crystalline material. Examples of crystalline materials that can be used as substrate 50 include, but are not limited to, silicon (Si), germanium (Ge), silicon germanium alloys (SiGe), silicon carbide (SiC), III-V compound semiconductors or II-VI compound semiconductors.

In some embodiments, substrate 50 may be a bulk crystalline substrate. The term "bulk" denotes the entirety of the crystalline substrate is composed of at least one crystalline material with no insulators and/or conductive materials present therein.

In yet other embodiments of the present application, substrate 50 may be a semiconductor-on-insulator (SOI) including, from bottom to top, a handle substrate, an insulator layer and a topmost crystalline semiconductor layer. In some embodiments, the handle substrate may be composed of one of the semiconductor materials mentioned above. In other embodiments, the handle substrate may be composed of a dielectric material or a conductive material. In yet other embodiments, the handle substrate may be omitted. The insulator layer of the SOI substrate may be composed of a dielectric oxide, dielectric nitride or a multilayered stack thereof. In one example, the insulator layer of the SOI substrate may be composed of silicon dioxide and/or silicon nitride. The topmost semiconductor layer of the SOI substrate may be composed of one of the semiconductor materials mentioned above. The SOI can be formed utilizing well known processes including, for example, a layer transfer process, or by a SIMOX (separation by ion implantation of oxygen) process. The topmost semiconductor layer must be at least partially crystalline in nature with the crystalline regions crystallographically related to one another.

The crystalline material that provides the substrate 50 may have any of the well known crystal orientations, including, for example, {100}, {110}, or {111}. In some embodiments of the present application, at least an upper portion of the semiconductor material that provides the substrate 50 is a single crystalline semiconductor material.

The substrate 50 also includes a plurality of spaced apart imageable ready regions 52. In accordance with the present application, the plurality of spaced apart imageable ready regions 52 are intentionally formed on the substrate 50. The term "imageable ready regions" denotes regions of a crystalline material that are present on known locations of the substrate 50 with specific material requirements and whose area is sufficient enough generate a sufficient portion of the electron channeling pattern or electron backscatter diffraction pattern for indexing or image matching. In some embodiments of the present application, each of the imageable ready regions 52 has both of the dimensions greater than 0.5 mm. Other areas are possible as long as the area of each of the imageable ready regions 52 can be imaged during a subsequently performed imaging step 104. The phrase "plurality of spaced apart imageable ready regions" denotes at least three imageable ready regions 52 that are of sufficient number and placement such that interpolating step 108 of FIG. 1 results in a map that is representative of the crystal orientation of the entire sample surface.

In some embodiments of the present application, the crystalline material that provides each imageable ready regions 52 may be a semiconductor material including one of the semiconductor materials mentioned above for substrate 50. In some embodiments, the semiconductor material that provides the crystalline material of each imageable ready region 52 may be the same as the substrate 50. In other embodiments, the semiconductor material that provides the crystalline material of each imageable ready region 52 may be different from the semiconductor material of the substrate 50.

In some embodiments of the present application, each imageable ready region 52 can be entirely composed of a crystalline material. In such an embodiment, each imageable ready region 52 can be formed by epitaxially growing (or depositing) a crystalline material on a crystalline semiconductor surface of substrate 50 and then patterning the epitaxial grown crystalline material to provide the imageable ready region 52.

The terms "epitaxial growth and/or deposition" and "epitaxially formed and/or grown" mean the growth of a material on a deposition surface of a material, in which the material being grown has the same crystalline characteristics such as orientation as the material of the deposition surface. In an epitaxial deposition process, the chemical reactants provided are controlled and the system parameters are set so that the depositing atoms arrive at the deposition surface of a material with sufficient energy to move around on the surface and orient themselves to the crystal arrangement of the atoms of the deposition surface. Therefore, an epitaxial material that is formed by an epitaxial deposition process has a crystalline orientation that is aligned with the crystalline orientation of the material of the deposition surface. For example, an epitaxial semiconductor material deposited on a {100} crystal surface can take on a {100} orientation. Examples of various epitaxial growth processes that are suitable for use in forming the silicon germanium alloy layer 14 L include, e.g., rapid thermal chemical vapor deposition (RTCVD), low-energy plasma deposition (LEPD), ultra-high vacuum chemical vapor deposition (UHVCVD), atmospheric pressure chemical vapor deposition (APCVD), molecular beam epitaxy (MBE) or metal-organic CVD (MOCVD). The temperature for epitaxial deposition typically ranges from 250° C. to 900° C.

The patterning of the epitaxially grown crystalline material used to provide the imageable ready regions 52 may include lithography and etching. Lithography includes forming a photoresist material (not shown) on the topmost surface of the epitaxally grown crystalline material. The photoresist material can be formed utilizing a deposition process such as, for example, spin-on coating, evaporation, or chemical vapor deposition. Following the deposition of the photoresist material, the photoresist material is exposed to a pattern of irradiation, and thereafter the exposed resist material is developed utilizing a conventional resist developer to provide a patterned photoresist material. At least one etch such as, for example, a reactive ion etch, can be used to complete the pattern transfer. Following at least one pattern transfer etch process, the patterned photoresist material can be removed from the structure utilizing a conventional resist stripping process such as, for example, ashing.

In some embodiments of the present application, each imageable ready region 52 comprises at least one patterned crystalline material structure such as, for example, a fin structure. As used herein, a "fin" is a structure that has a first pair of sidewalls along a lengthwise direction that is longer than a second pair of sidewalls along a widthwise direction. In such an embodiment, each imageable ready region 52 may be formed by epitaxially growing (or depositing) a crystalline material (as defined above) on a crystalline semiconductor surface of substrate 50 and then patterning the epitaxial grown crystalline material to provide the patterned crystalline material structures. Patterning may be achieved by lithography and etch, as defined above, a sidewall image transfer (SIT) process, or a by a direct self-assembly (DSA) process. In a typical SIT process, spacers are formed on sidewalls of a sacrificial mandrel. The sacrificial mandrel is removed and the remaining spacers are used as a etch mask. The spacers are then removed after etching. DSA uses block copolymers that can phase separate during an anneal process. Each first phase separate block can then be removed, while maintaining second phase separated blocks as an etch mask.

Alternatively, and in another embodiment of the present application, the at least one patterned crystalline material structure can be formed by patterning an upper crystalline semiconductor material surface of the substrate 50. Patterning may be achieved by lithography and etching, SIT or DSA.

In some embodiments of the present application, the imageable ready region 52 can contain an amorphous material that is deposited over, or in between, the patterned crystalline material of each imageable ready region 52. The term "amorphous material" denotes a material that lacks a long range crystal order. In one example, the amorphous material may be composed of a dielectric oxide such as, for example, silicon dioxide, or a dielectric nitride such as, for example, silicon nitride. In such an embodiment, the amorphous material may be no more thick than is necessary to view the electron channeling pattern. The amorphous material may be formed utilizing any well known deposition process such as, for example, chemical vapor deposition (CVD) or chemical enhanced chemical vapor deposition (CVD). A material removal process such as, for example, planarization, recessing, or patterning may follow the deposition of the amorphous material.

In some embodiments of the present application, for example, the thickness of amorphous $SiO_2$ on Si can be no more than 50 nm thick using a nominal 20 kV electron beam with a nominal probe current in the nanoampere range. The amorphous material that is formed between the patterned crystalline material structures can have variable thickness, while the amorphous material formed above the patterned crystalline material structures can have a thickness of less than 50 nm. In such an embodiment, the amorphous material that is present in between the patterned crystalline material structures should cover an area of the imageable ready region 52 less than required to obtain a channeling pattern.

As is further shown in FIG. 2, at least one device area 54 surrounds each of the imageable ready regions 52. The at least one devices area 54 contains a crystalline material in which defects need to be imaged. In some embodiments, the crystalline material that provides the at least one device area 54 may include one of the semiconductor materials mentioned above for the substrate 50. In some embodiments, the semiconductor material that provides the crystalline material of at least one device area 54 may be the same as the substrate 50. In other embodiments, the semiconductor material that provides the crystalline material of at least one device area 54 may be different from the semiconductor material of the substrate 50. The semiconductor material that provides the crystalline material of at least one device area 54 may be the same as, or different from, the semiconductor material that provides each imageable ready region 52.

In one embodiment and for EBSD, each imageable ready region has at least one dimension that is longer than 1 nm. In another embodiment and for ECP, each imageable ready region has at least one dimension that is longer than 0.1 mm.

In some embodiments of the present application, the at least one device area 54 can be formed by epitaxially growing a semiconductor material on the surface of the substrate 50 and then forming the imageable ready regions 52 thereon. In other embodiments, the at least one device area 54 represent a remaining portion of the substrate 50 after forming the patterned crystalline material structures that provide the imageable ready regions 52.

After providing the substrate 50 as shown in FIG. 2, an image of the electron channeling pattern (ECP) or electron backscatter diffraction pattern of each imageable ready region 52 is acquired using conventional techniques known to those skilled in the art such as scanning an electron beam and acquiring the backscatter or secondary electron signal. See, for example, step 104 of FIG. 1. The crystalline substrate is loaded into the microscope in a manner such that the orientation is approximately known through the use of the wafer flat or a crystallographic cleavage plane. The electron beam, after being impinged upon the substrate 50, interacts with the crystalline material of the imageable ready regions 52 to generate signals that can be later detected using suitable detectors. For example, the electron beams can interact with the crystalline material of each imageable ready regions 54 present on substrate 50 to generate respective backscattered electrons and a backscatter electron detector is used to detect these electrons. The ECP image or the electron backscatter diffraction pattern can be stored on a computer or processors as known to those skilled in the art.

Figure 3:
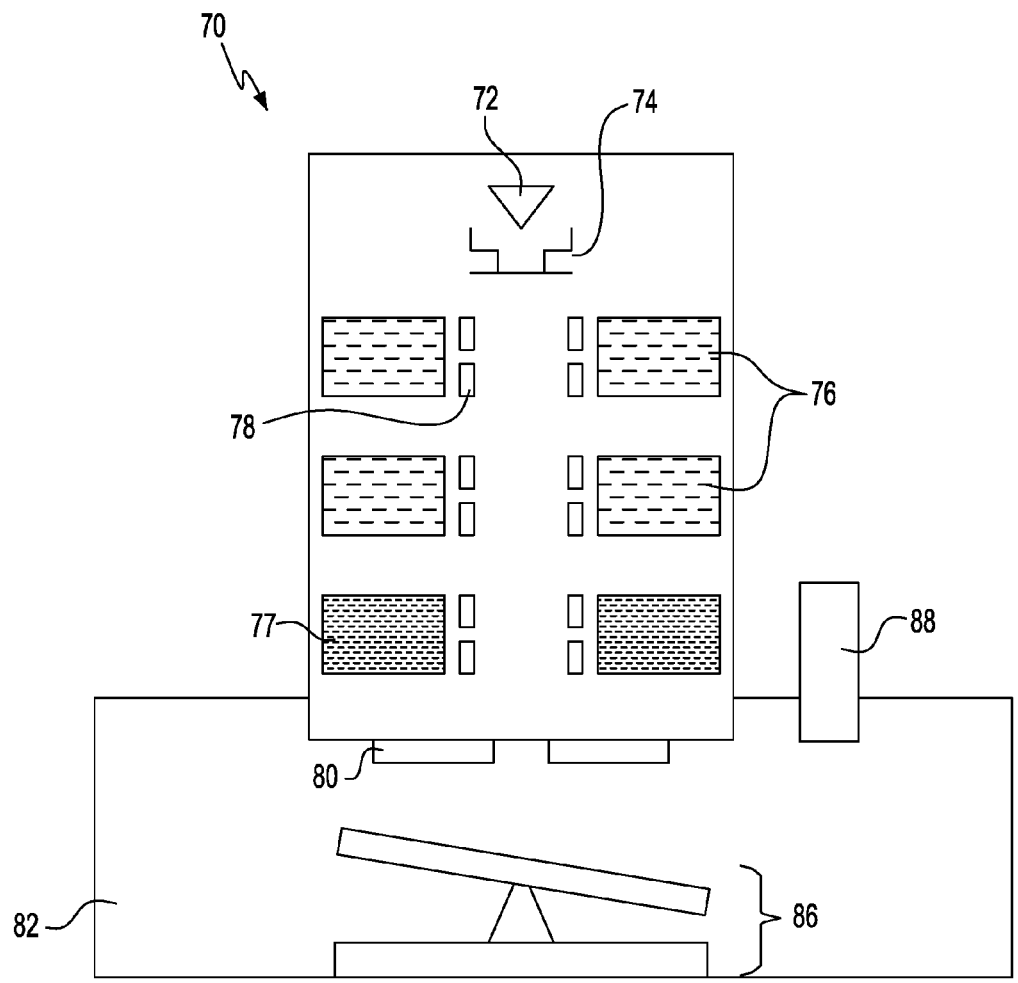
FIG. 3 is a schematic of an ECCI apparatus that can be used in the present application.

One such apparatus that can be used for electron channel pattern (ECP) imaging is shown in FIG. 3. Notably, FIG. 3 shows an apparatus 70 that contains an electron source 72 located within a probe (i.e., microscope). The probe also includes electrostatic lens 74, a plurality of condenser lenses 76, objective lenses 77 and deflection coils 78. Detectors 80 are located at the end of the probe. In some embodiments, detectors 80 may be backscatter electron detectors. The apparatus 70 further includes a sample chamber 82 and a sample holder 86 that may be tilted as shown. Another detector 88 may also be present. In some embodiments, detector 88 may be a secondary detector. The apparatus 70 shown in FIG. 3 and the conditions that are required to use the same are well known to those skilled in the art.

Figure 4:
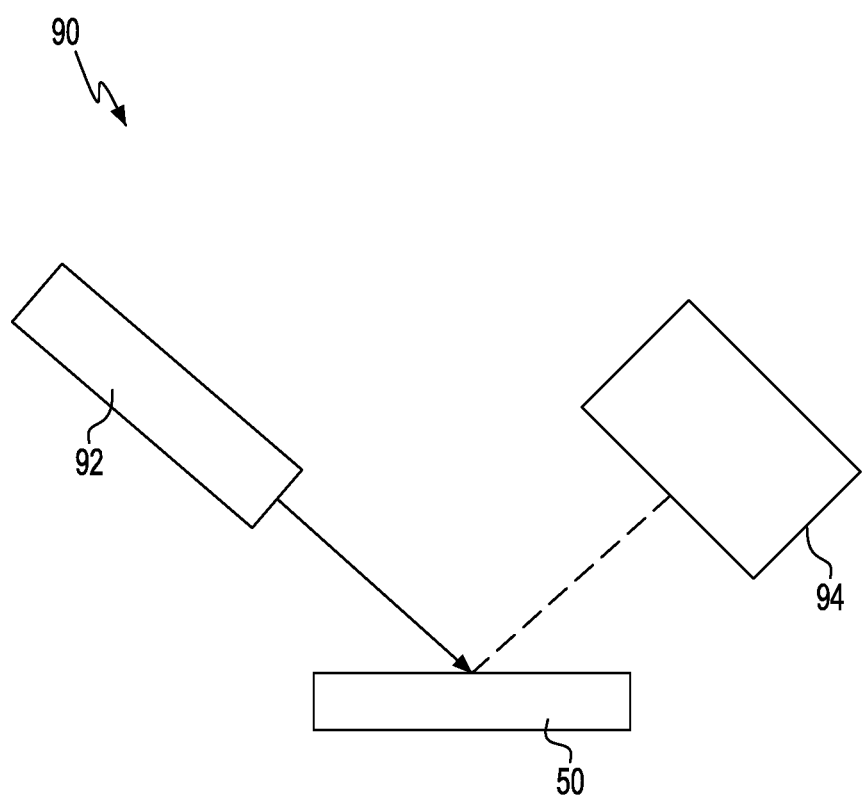
FIG. 4 is a schematic of an electron backscatter diffraction (EBSD) apparatus that can be employed in the present application.

In other embodiments of the present application, imaging of the electron backscatter diffraction pattern may be obtained utilizing electron backscatter diffraction (EBSD). FIG. 4 illustrates a simplified EBSD apparatus 90 that may be employed in the present application. The simplified EBSD apparatus 90 includes a probe 92 that contains an electron beam source that generates an electron beam. The probe 92 may include other elements such as, for example, electrostatic lens, a plurality of condenser lenses, objective lenses and deflection coils as mentioned above for the apparatus shown in FIG. 3. When EBSD imaging is used, the probe is tilted relative to the surface of the substrate 50 such that the electron beam impinges at an angle on the surface of substrate 50. The backscatter electron beam is then sensed by detector 94. The apparatus 90 shown in FIG. 4 and the conditions that are required to use the same are well known to those skilled in the art.

After imaging, an optimum channeling angle at each imageable ready region 52 is calculated, using a first algorithm. See, step 106 of FIG. 1. The calculating, using the first algorithm, may be performed using a computer or processor.

In one embodiment of the present application, the calculating using the first algorithm comprises determining the optimum channeling angle for each imageable ready region 52. In such an embodiment, analysis of the electron channeling pattern or the electron backscatter diffraction pattern of each of the imageable ready regions 52 is performed which identifies straight lines or kikuchi bands in the image using a 2D-Hough transform, and compares it to a crystallographic database to find one or more solutions for plane indices. A detailed reference for the steps to obtain the indices of the kikuchi bands is outlined in Wright, Stuart I. "Fundamentals of automated EBSD" Electron Backscatter Diffraction in Materials Science, Springer US, 2000, 51-64. Either the orientation of the substrate 50, or the electron beam is then tilted such that the desired kikuchi band is centered along the optic axis of the microscope to within 0.1 degrees, providing optimum channeling angle.

In another embodiment of the present application, the calculating using the first algorithm comprises tilting and rotating the substrate 50 and acquiring an image of the electron channeling patterns at an imageable ready region 52 at a series of different substrate-beam angles. An example of the above is obtaining electron channeling patterns at intervals of 0.05 degrees of tilt and rotation of the substrate 50. These images are compared to a reference image of an aligned electron channeling pattern. The tilt and rotation angle at which the electron channeling pattern most resembles the reference image and such that the final error in the orientation is less than 0.1 degrees, is designated as the optimum channeling angle for the imageable ready region 52 in question. In one embodiment of the present application, substrate-beam angle can be changed at intervals of tilt and rotation of the substrate ranging from 0.05 degree to 1 degree such that the final angular error between the electron channeling pattern or the electron backscatter diffraction pattern and the reference image is less than 0.1 degrees.

Determination of the image which most resembles the reference image can be performed using conventional image matching techniques such as scale-invariant feature transform (SIFT) or speeded up robust features (SURF). In such imaging matching techniques, it is not necessary to index the kikuchi bands. One such image matching technique is disclosed, for example, in U.S. Pat. No. 6,711,293, the entire content of which is incorporated by reference.

The optimum channeling condition of the crystalline material present in the at least one device area 54 between and around each imageable ready region 52 is then interpolated, using a second algorithm. See, step 108 of FIG. 1. For example, an interpolation scheme is set up for both the tilt and rotation axis for the optimum channeling angle. The difference in optimum channeling angle between the imageable ready regions 52 is anticipated to be small (less than 0.5 degrees) except in cases involving extensive processing that induces crystalline substrate bow. The accuracy of the interpolation can be sensitive to the total number of imageable ready regions 52.

The second algorithm that can be used in the present application includes, but is not limited to, a nearest neighbor technique, a linear technique, a polynomial technique, a spline technique or any combination thereof. The fit to the necessary function can be obtained using a error minimization algorithm such as Levenberg-Marquardt. Such a scheme could be applied independently to the tilt and rotation axis of the sample stage supporting substrate 50. The interpolating, using the second algorithm may be performed using a computer or processor.

Figure 5:
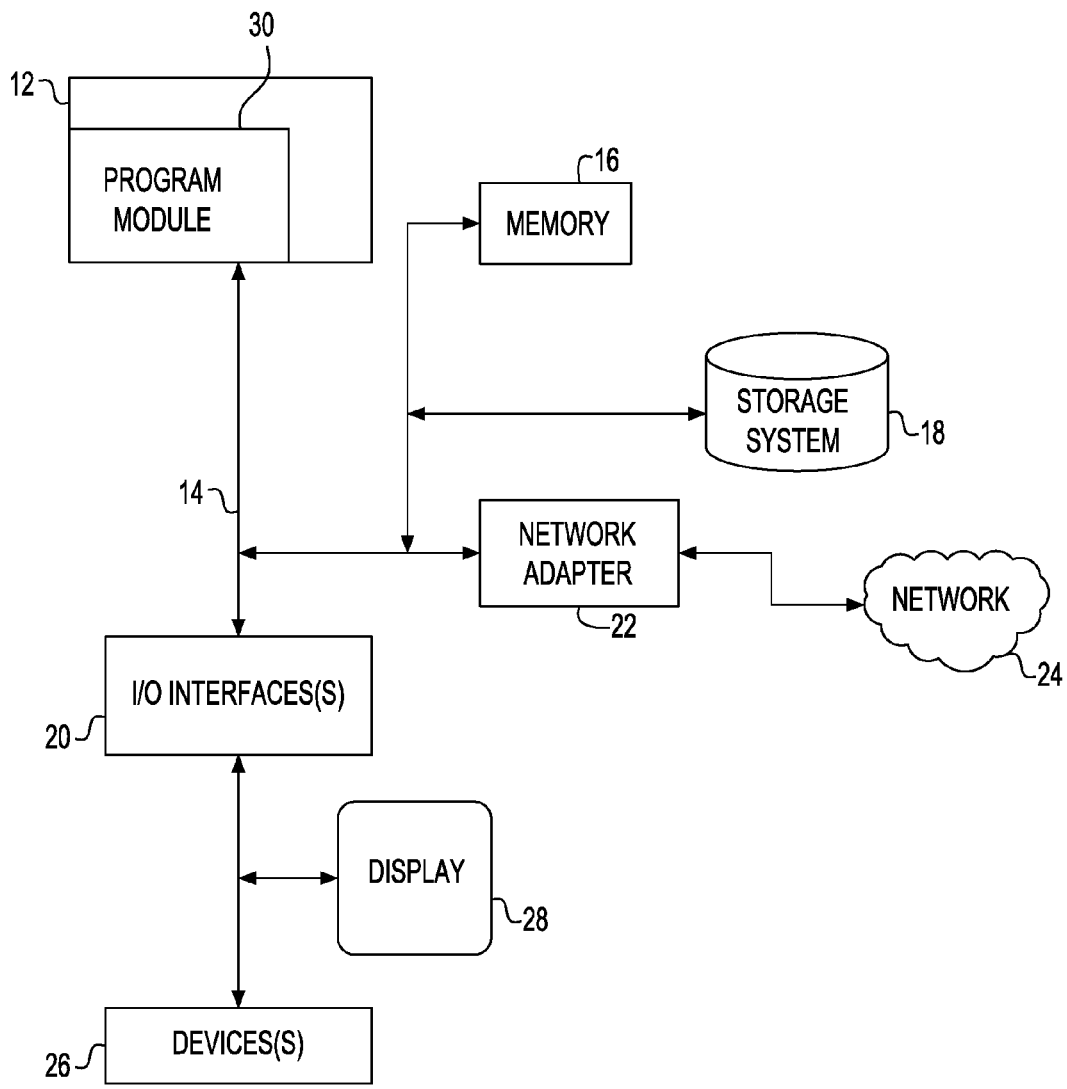
FIG. 5 is a schematic of an exemplary computer or processing system that may be used in the present application.

Referring now to FIG. 5, there is illustrated a schematic of an example computer or processing system that may be used with the method of the present application. The computer or processing system may perform the various algorithms mentioned above and may be connected and used in connection with any of the apparatuses mentioned above. The computer system is only one example of a suitable processing system and is not intended to suggest any limitation as to the scope of use or functionality of embodiments of the methodology described herein. The processing system shown may be operational with numerous other general purpose or special purpose computing system environments or configurations. Examples of well-known computing systems, environments, and/or configurations that may be suitable for use with the processing system shown in FIG. 5 may include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

The computer system may be described in the general context of computer system executable instructions, such as program modules, being executed by a computer system. Generally, program modules may include routines, programs, objects, components, logic, data structures, and so on that perform particular tasks or implement particular abstract data types. The computer system may be practiced in distributed cloud computing environments where tasks are performed by remote processing devices that are linked through a communications network. In a distributed cloud computing environment, program modules may be located in both local and remote computer system storage media including memory storage devices.

The components of computer system may include, but are not limited to, one or more processors or processing units 12, a system memory 16, and a bus 14 that couples various system components including system memory 16 to processor 12. The processor 12 may include a program module 30 that performs the calculating and interpolating described herein. The program module 30 may be programmed into the integrated circuits of the processor 12, or loaded from memory 16, storage device 18, or network 24 or combinations thereof.

Bus 14 may represent one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

The computer system may include a variety of computer system readable media. Such media may be any available media that is accessible by computer system, and it may include both volatile and non-volatile media, removable and non-removable media.

System memory 16 can include computer system readable media in the form of volatile memory, such as random access memory (RAM) and/or cache memory or others. Computer system may further include other removable/non-removable, volatile/non-volatile computer system storage media. By way of example only, storage system 18 can be provided for reading from and writing to a non-removable, non-volatile magnetic media (e.g., a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 14 by one or more data media interfaces.

The computer system may also communicate with one or more external devices 26 such as a keyboard, a pointing device, a display 28, etc.; one or more devices that enable a user to interact with computer system; and/or any devices (e.g., network card, modem, etc.) that enable computer system to communicate with one or more other computing devices. Such communication can occur via Input/Output (I/O) interfaces 20.

Still yet, computer system can communicate with one or more networks 24 such as a local area network (LAN), a general wide area network (WAN), and/or a public network (e.g., the Internet) via network adapter 22. As depicted, network adapter 22 communicates with the other components of computer system via bus 14. It should be understood that although not shown, other hardware and/or software components could be used in conjunction with computer system. Examples include, but are not limited to: microcode, device drivers, redundant processing units, external disk drive arrays, RAID systems, tape drives, and data archival storage systems, etc.

Some of the processing steps of the present application may be a system, a method, and/or a computer program product. The computer program product may include a computer readable storage medium (or media) having computer readable program instructions thereon for causing a processor to carry out aspects of the present application.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present application may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present application.

Aspects of the present application are described herein with reference to flowchart illustrations and/or block diagrams of methods, apparatus (systems), and computer program products according to embodiments of the application. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

Parts of the flowcharts and block diagrams in the drawings illustrate the architecture, functionality, and operation of possible implementations of systems, methods, and computer program products according to various embodiments of the present application. In this regard, some of the blocks in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the present application has been particularly shown and described with respect to preferred embodiments thereof, it will be understood by those skilled in the art that the foregoing and other changes in forms and details may be made without departing from the spirit and scope of the present application. It is therefore intended that the present application not be limited to the exact forms and details described and illustrated, but fall within the scope of the appended claims.

What is claimed is:

1. A method for automatic alignment that increases the throughput of electron channeling contrast imaging (ECCI), said method comprising:
providing a substrate intentionally containing a plurality of spaced apart imageable ready regions capable of generating an electron channeling pattern or electron backscatter diffraction pattern surrounded by at least one device area containing a crystalline material that has a crystallographic orientation that is aligned to the material of each of said imageable ready regions;
obtaining an image of the electron channeling pattern and/or electron backscatter diffraction pattern of each imageable ready region;
calculating, using a first algorithm, an optimum channeling angle at each imageable ready region; and
interpolating, using a second algorithm, said optimum channeling angle between and around each imageable ready region to compute the optimum channeling angle for the crystalline material present in the at least one device area.

2. The method of claim 1, wherein each imageable ready region for has at least one dimension that is longer than 1 nm for electron backscatter diffraction (EBSD).

3. The method of claim 1, wherein each imageable ready region has at least one dimension that is longer than 0.1 mm for ECP.

4. The method of claim 1, wherein each imageable ready region is entirely composed of a crystalline material.

5. The method of claim 1, wherein each imageable ready region is composed of a crystalline material with an amorphous material present on an upper surface thereof.

6. The method of claim 5, wherein said an amorphous material present on said upper surface of each imageable ready region has a thickness less than that necessary to obscure an electron channeling pattern.

7. The method of claim 1, wherein each imageable ready region comprises at least one patterned crystalline material structure.

8. The method of claim 7, wherein a region between said at least one patterned crystalline material structure can contain an amorphous material.

9. The method of claim 8, wherein said amorphous material formed between said at least one patterned crystalline material structure covers no more than the area than that necessary to obtain an electron channeling pattern.

10. The method of claim 1, wherein said obtaining said image of each imageable ready region comprises collecting an electron channeling pattern (ECP).

11. The method of claim 1, wherein said obtaining said image of each imageable ready region comprises collecting an electron backscatter diffraction (EBSD) pattern.

12. The method of claim 1, wherein said calculating, using said first algorithm, comprises:
identifying straight channeling lines; and
comparing said straight channeling lines to a crystallographic database to find one or more solutions for plane indices.

13. The method of claim 1, wherein said calculating, using said first algorithm, comprises:
identifying Kikuchi bands; and
comparing said Kikuchi bands to a crystallographic database to find one or more solutions for plane indices.

14. The method of claim 1, wherein said calculating, using said first algorithm, comprises:
acquiring an image of said electron channel patterns at each imageable ready region at a series of different substrate-beam angles; and
comparing said images to a reference image of an aligned electron channeling pattern.

15. The method of claim 14, wherein said substrate-beam angle is changed using tilt and rotation of the substrate such that the final angular error between the said pattern and the reference image is less than 0.1 degrees.

16. The method of claim 14, wherein said comparing comprising an imaging matching technique.

17. The method of claim 1, wherein said calculating, using said first algorithm, comprises:
acquiring an image of said EBSD pattern at each imageable ready region at a series of different substrate-beam angles; and
comparing said images to a reference image of an aligned EBSD pattern.

18. The method of claim 17, wherein said substrate-beam angle is changed using tilt and rotation of the substrate such that the final angular error between the said pattern and the reference image is less than 0.1 degrees.

19. The method of claim 17, wherein said comparing comprising an imaging matching technique.

20. The method of claim 1, wherein said second algorithm comprises a nearest neighbor technique, a linear technique, a polynomial technique, a spline technique or any combination thereof.

\* \* \* \* \*